United States Patent [19]

Suzuki et al.

[11] Patent Number: 4,861,521
[45] Date of Patent: Aug. 29, 1989

[54] POLYMERIZABLE LIPOSOME-FORMING LIPID, AND METHOD FOR PRODUCTION THEREOF

[75] Inventors: Kazuhiko Suzuki; Hiroshi Yoshioka, both of Fujinomiya, Japan

[73] Assignee: Terumo Corporation, Tokyo, Japan

[21] Appl. No.: 73,175

[22] Filed: Jul. 14, 1987

Related U.S. Application Data

[63] Continuation-in-part of Ser. No. 813,540, Dec. 26, 1985, abandoned.

[30] Foreign Application Priority Data

Dec. 28, 1984 [JP] Japan .................. 59-274894
Dec. 28, 1984 [JP] Japan .................. 59-274895

[51] Int. Cl.⁴ .................................. C07F 9/10
[52] U.S. Cl. ...................... 260/403; 204/157.44
[58] Field of Search ................................ 260/403

[56] References Cited

FOREIGN PATENT DOCUMENTS 186211 7/1986 European Pat. Off. ............ 260/403

Primary Examiner—Anton H. Sutto
Attorney, Agent, or Firm—Burns, Doane, Swecker & Mathis

[57] ABSTRACT

A polymerizable liposome-forming lipid represented by the following general formula I:

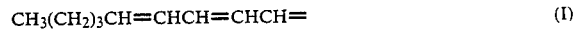
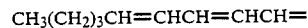
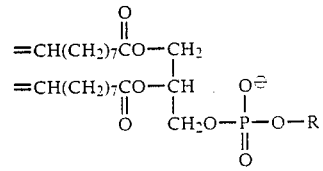

wherein R stands for $-(CH_2)_2N^{\oplus}(CH_3)_3$, $-(CH_2)_2N^{\oplus}H_3$ or $-CH_2-CH(N^{\oplus}H_3)-COO^{\ominus}$.

4 Claims, 1 Drawing Sheet

POLYMERIZABLE LIPOSOME-FORMING LIPID, AND METHOD FOR PRODUCTION THEREOF

RELATED APPLICATION

This application is a continuation-in-part of our copending application, Ser. No. 813,540, filed Dec. 26, 1985, now abandoned.

BACKGROUND OF THE INVENTION

1. Field of the Invention

This invention relates to a novel polymerizable liposome-forming lipid, a method for the production thereof, and use thereof. More particularly, this invention relates to a polymerizable liposome-forming lipid capable of forming polymerized liposomes of excellent stability and to a method for the production thereof. This invention relates further to a novel medical carrier.

2. Description of Prior Art

At various efforts are being made to encapsulate medicinal substances, enzymes, etc. in microcapsules and offer the filled microcapsules as medicines. The microcapsules filled with hemoglobin serve as artificial red cells.

The microcapsulation, in the early stage of its development, relied on the capsulation of a high molecular compound by emulsification or on the capsulation by surface polycondensation entailing the formation of a polymer (polyamide). These conventional methods, however, have posed problems such as the inclination toward induction of thrombosis and other disorders which are fatal to the adoption of microcapsulated preparations as medicines, because the polymers as the materials for capsulation are poisonous, the organic solvents inevitably used during the synthesis of such polymers and suffered to remain in the produced capsules are poisonous, and the capsules have a large particle size (several $\mu$m to 1,000 $\mu$m).

Incidentally, the microcapsulation of medicinal substances, enzymes, hemoglobin, etc. is mainly aimed at enabling the medicinal substances, enzymes, hemoglobin, etc. which are unstable in vivo to retain their activities for a long time and allowing their effects to last long.

For a microcapsulating material to be admitted for in vivo application or for preparation of a medicine, it is required to manifest only minimal toxicity to the living body, permit sufficient reduction in the particle diameter of capsules, and enable the capsules to enjoy ample stability in vivo.

The liposomes which are fine spherical compartments formed in water by oriented aggregation of various phospholipids, the main components for living membranes, satisfies these conditions fairly well. The potentiality of utility of the liposome as a microcapsulating material, therefore, has come to arrest growing attention.

The liposomes which use natural phospholipids as they are, however, have a short life and manifest poor stability in its interaction particularly with living cells. In the field of drug deliveries which are utilized as carriers for supporting medicines within the liposomes, and of model studies on recognition or interaction between cells, therefore, numerous studies are now under way in search of stable liposomes. At present, the most efficient approach to the stabilization resides in polymerization of the existing liposomes.

The polymerization of the liposomes are aimed at stabilizing the lipid bilayer membranes and consequently the structure of vesicle structure through the medium of the covalent bond of lipid molecules. This stabilization is preponderantly attained by a procedure which comprises incorporating a polymerizable functional group into the lipid molecule thereby preparing monomeric liposomes and thereafter causing polymerization of the lipid within the membrane of the liposomes. A typical version of this method, as described in J. Am. Chem. Soc., 106, 1627–1633 (1984), for example, involves first synthesizing an unsaturated fatty acid and then esterifying the unsaturated fatty acid with the hydrolyzate of a phospholipid thereby incorporating a polymerizable reactive group into the phospholipid. In accordance with this method, however, the synthesis of the unsaturated fatty acid calls for a great deal of time and labor and the isolation of the product of synthesis turns out to be an extremely complicated work, and the polymerizable phospholipid is obtained as the final product in a yield of only several percent as reported in the literature. The inventors, by faithfully repeating the experiment reported, obtained the phospholipid in a yield about one tenth of the yield reported in the literature.

Attempts are being made also to utilize liposomes as the material for the artificial red cells obtainable by microcapsulation of hemoglobin. It is expected that leakage of hemoglobin into blood plasma which is a serious problem to the liposome formed solely of natural phospholipid will be effectively curbed by utilizing polymerized liposomes using polymerizable phospholipids.

A few problems, however, stand on the way to successful utility of the polymeric liposomes as a material for the artificial blood. Firstly, since the polymerizable phospholipids are synthesized purely organic chemically through a multiplicity of serial reactions on the basis of extremely elaborate molecular design, it cannot be easily synthesized in a large volume from the practical point of view and cannot help being extremely expensive. Secondly, the method of polymerization for producing the polymeric liposomes have much to be desired. Generally, the reaction for polymerization of the polymerizable phospholipids is carried out by using a radical polymerization initiator or ultraviolet light. The method using the initiator, however, is undesirable where the product of polymerization is intended for in vivo application because the method generally requires application of heat and also because the initiator persists in the produced liposomes. The method resorting to ultraviolet light has the disadvantage that the hemoglobin in the capsules is susceptible to denaturation because the conventional phospholipids are not sufficiently polymerizable and are required to be amply irradiated.

An object of this invention, therefore, is to provide a novel polymerizable liposome-forming lipid and a method for the production of the lipid.

Another object of this invention is to provide excellently stable polymeric liposomes and a method for the production of the lipid.

Yet another object of this invention is to provide polymeric liposome-forming lipids such that the monomeric liposome formed of the lipid is easily polymerized under mild conditions and a method for the production of the lipid.

Still another object of this invention is to provide a novel medical carrier.

A further object of this invention is to provide a medical carrier made of excellently stable polymeric liposome-forming lipids.

Another object of this invention is to provide a medical carrier suffering from only nominal leakage of a carried substance.

Still another object of this invention is to provide a medical carrier useful for microcapsulation of hemoglobin, for example.

SUMMARY OF THE INVENTION

The objects described above are attained by a polymerizable liposome-forming lipid represented by the following general formula I.

$$CH_3(CH_2)_3CH=CHCH=CHCH= \quad (I)$$
$$CH_3(CH_2)_3CH=CHCH=CHCH=$$

$$=CH(CH_2)_7\overset{O}{\overset{\|}{C}}O-CH_2$$
$$=CH(CH_2)_7\overset{\|}{\underset{O}{C}}O-\overset{|}{C}H \quad O^\ominus$$
$$CH_2O-\overset{\|}{\underset{O}{P}}-O-R$$

wherein R stands for $-(CH_2)_2N^\oplus(CH_3)_3$, $-(CH_2)_2N^\oplus H_3$, or $-CH_2-CH(N^\oplus H_3)-COO^\ominus$.

This invention also relates to a polymerizable liposome-forming lipid having $-CH_2)_2N^\oplus(CH_3)_3$ as the substituent R in the general formula.

The objects are also attained by a method for the production of a polymerizable liposome-forming lipid represented by the general formula I, which method is characterized by esterifying tung oil fatty acid containing at least 60% by weight of olesstearic acid with the hydrolyzate of phospholipid.

Further, this invention relates to a method for the production of a polymerizable liposome-forming lipid, wherein the tung oil fatty acid is used in the form of an acid anhydride in an amount of 200 to 400 parts by weight based on 100 parts by weight of the hydrolyzate of phospholipid. This invention also relates to a method for the production of a polymerizable liposome-forming lipid, wherein the esterification is carried out at a temperature in the range of 15° to 25° C. This invention relates further to a method for the production of a polymerizable liposome-forming lipid, wherein the hydrolyzate of lipid is the hydrolyzate of egg yolk lecithin. Further, this invention relates to a method for the production of a polymerizable liposome-forming lipid, wherein the oleostearic acid content in the tung oil fatty acid is at least 60% by weight.

The various objects described above are accomplished by a medical carrier produced by irradiating with ultraviolet light or radiation liposomes having as a principal component thereof of a liposome-forming lipid represented by the following general formula I.

$$CH_3(CH_2)_3CH=CHCH=CHCH= \quad (I)$$
$$CH_3(CH_2)_3CH=CHCH=CHCH=$$

-continued
$$=CH(CH_2)_7\overset{O}{\overset{\|}{C}}O-CH_2$$
$$=CH(CH_2)_7\overset{\|}{\underset{O}{C}}O-\overset{|}{C}H \quad O^\ominus$$
$$CH_2O-\overset{\|}{\underset{O}{P}}-O-R$$

wherein R stands for $-(CH_2)_2N^\oplus(CH_3)_3$, or $-CH_2-CH(N^\oplus H_3)-COO^\ominus$.

Further, this invention relates to a medical carrier having $-(CH_2)_2N^\oplus(CH_3)_3$ as the substituent R in the general formula. This invention relates also to a medical carrier, produced by effecting the irradiation with ultraviolet light. This invention further relates to a medical carrier to be used for supporting hemoglobin.

EXPLANATION OF THE PREFERRED EMBODIMENT

Figure 1:
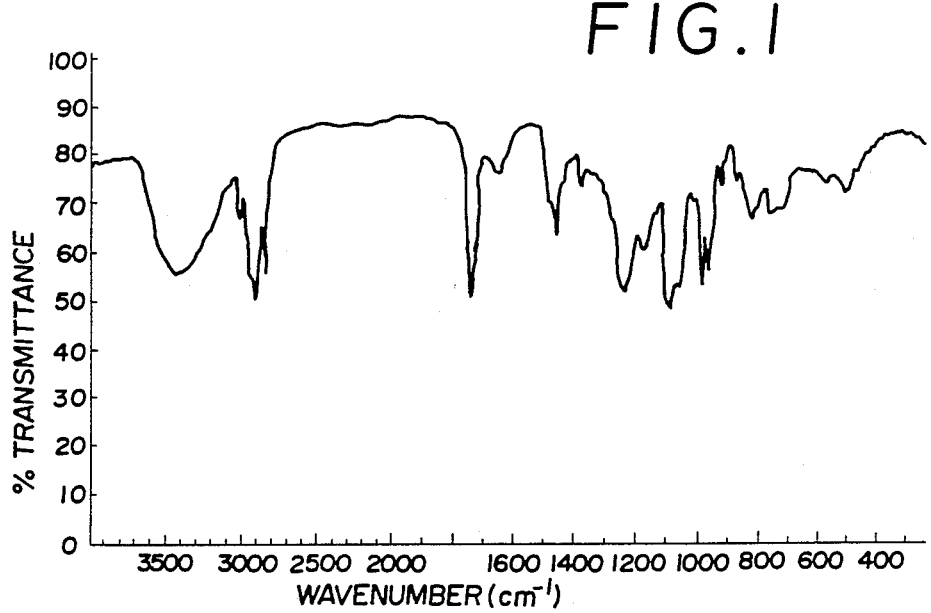
FIG. 1 is a chart showing a typical infrared absorption spectrum of a polymerizable liposome-forming lipid of the present invention.
Figure 2:
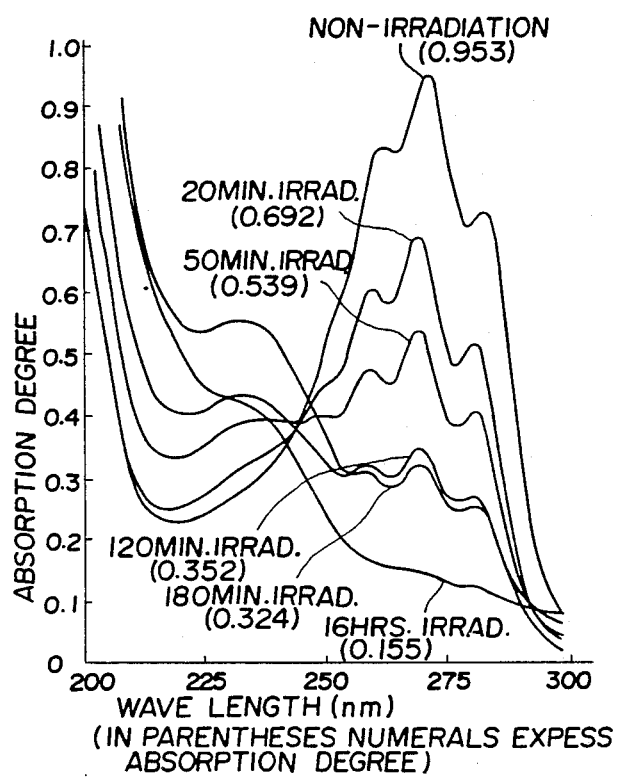
FIG. 2 is a chart showing a typical ultraviolet absorption spectrum illustrating the degree of polymerization obtained by the irradiation with ultraviolet light in the production of liposomes from a liposome-forming lipid of the present invention.

The phospholipid to be used in this invention is one kind of complex lipid, i.e. a living body component formed by the combination of fatty acid and phosphoric acid with alcohols. In terms of chemical structure, it comprises two moieties, i.e. a nonpolar moiety formed of a relatively long aliphatic hydrocarbon and a polar moiety formed of phosphoric acid and bases. When this phospholipid is dispersed in water, there is formed small vesicles having the structure of a bilayer membranes. These small vesicles are liposomes. Examples of the phospholipid of this behavior include egg yolk lecithin (phosphatidyl choline), cephalin, and phosphatidyl serine. The egg yolk lecithin is the most desirable choice.

The phosphatidyl choline is represented by the following general formula II.

$$R_1COOCH_2 \quad (III)$$
$$R_2COOCH \quad O^\ominus$$
$$CH_2-O-\overset{\|}{\underset{O}{P}}-OCH_2CH_2N^\oplus(CH_3)_3$$

The liposome formed from these phospholipids have a short life and entails a problem from the standpoint of practical utility. This invention effects synthesis of a polymerizable phospholipid by substituting the fatty acid parts ($R_1$ and $R_2$) of a phospholipid with oleostearic acid, a natural unsaturated fatty acid, thereby introducing polymerizable reactive groups into the phospholipid.

The oleostearic acid to be used in this invention is an unsaturated fatty acid having conjugated double bonds at the 9, 11, 13 positions as shown by the following chemical formula III. In tung oil, it exists in the form of glyceride and accounts for 80 to 95% by weight of the mixed fatty acids. The tung oil fatty acid obtained by hydrolyzing the tung oil contains at least 60% by weight, preferably at least 80% by weight of oleostearic acid and the balance of saturated acid, oleic acid, linolic acid, etc. This tung oil fatty acid may be used in its unmodified form as a natural unsaturated fatty acid. Optionally, it may be refined as by column chromatography or recrystallization to isolate oleostearic acid.

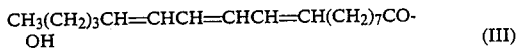

Generally, this tung oil fatty acid is subjected in the form of acid anhydride to esterification. The amount of the tung oil fatty acid to be used in the range of 200 to 400 parts by weight, preferably 300 to 370 parts by weight, based on 100 parts by, weight of the phospholipid.

The aforementioned phospholipid is used in the form of a hydrolyzate, particularly in the form of metal complex such as, for example, the complex of such a metal as cadmium.

The reaction of esterification is carried out as follows. In a medium such as chloroform, carbon tetrachloride, or methylene chloride, the hydrolyzate of the phospholipid or the metal complex thereof is stirred and suspended. In this suspension, the tung oil fatty acid anhydride and a catalyst are placed and, after the interior of the reaction system has been displaced with an inert gas such as argon, nitrogen, or helium, subjected to reaction in a dark place at a temperature in the range of 15° to 25° C., preferably 18° to 22° C., for 24 to 72 hours, preferably 40 to 72 hours. A typical catalyst is 4-dimethylaminopyridine, for example. It is used in an amount of 45 to 90 parts by weight, preferably 68 to 84 parts by weight based on 100 parts by weight of the hydrolyzate of phospholipid. Then, the reaction mixture is filtered to remove white insolubles precipitated during the reaction and subjected to evaporation at room temperature to expel the solvent. The residue is dissolved in a mixed solvent of chloroform, methanol, and water (mixing ratio 4/5/1). This solution is brought into contact with an ion exchange resin and the adsorbate is eluted. The eluate is subjected to evaporation, and then the residue is dissolved in a small amount of chloroform, and refined by silica gel column with a mixed solution of chloroform and methanol.

The liposome-forming lipid to be obtained is variable with the kind of phospholipid to be used. When yolk lecithin is used, for example, there is obtained oleostearic acid phosphatidyl choline represented by the chemical formula (IV). When cephalin or phosphatidyl serine is used, there is obtained a corresponding liposome-forming lipid.

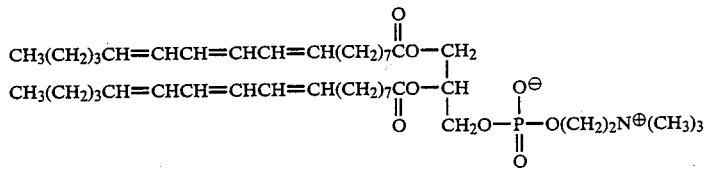

The liposome-forming lipid so obtained is dissolved in a solvent such as chloroform, methylene chloride, ether, or methanol. The lipid solution is placed in a round-bottm container and treated for the solvent to be wholly expelled by evaporation and for the lipid to be deposited in the form of thin layer on the round bottom of the container. The lipid layer and phosphate buffer or Hepes buffer added thereto are shaken with a mixer and subjected to an ultrasnic treatment under an atmosphere of inert gas such as argon, nitrogen, or helium. Consequently, there is obtained monomeric liposomes. The monomeric liposmes can be used as a carrier for medicinal substances, enzymes, hemoglobin etc.

When the monomeric liposomes obtained as described above are irradiated with ultraviolet light or radiation such as gamma ray or electron beam, particularly with ultraviolet light, the three conjugated double bonds in the two aliphatic groups are easily polymerized to give rise to polymerized liposomes. By this polymerization, the stability of liposomes are increased. The polymerized liposomes can also be used as a carrier for medicinal substances, enzymes, hemoglobin and the like.

When the substance to be carried is of a hydrophilic type, it is deposited as sealed in the inner aqueous compartment of the monomeric or polymerized liposomes. When the substance is of a hydrophobic type, it is deposited on the aliphatic part, of the monomerric or polymerized liposomes.

Various methods are available for the deposition of a given substance on the carrier under discussion. The deposition on the monomeric liposomes can be attained by mixing the polymerizable liposome-forming lipid with the aforementioned substance given to be carried, subjecting the resultant mixture to an ultrasonic treatment thereby forming a suspension of the monomeric liposomes, and centrifuging the suspension. The polymeric liposomes carrying the aforementioned substance thereon can be obtained by irradiating the monomeric liposomes having the substance deposited thereon as described above with ultraviolet light or with radiation.

The conditions for the irradiation are variable with the kind of the source of light. The irradiation with ultraviolet light, for example, is attained by placing the monomeric liposome suspension in a container pervious to ultraviolet light such as a container made of quartz glass, evacuating the container or displacing the interior of the container with an inert gas such as argon, nitrogen, or helium, setting a light source such as a mercury vapor lamp or a xenon lamp capable of emitting ultraviolet light at a distance of 5 to 20 cm, preferably 10 to 15 cm, from the container, and exposing the suspension to the ultraviolet light source for a period of 15 minutes to 16 hours, preferably 2 to 12 hours while keeping the suspension cooled with water or air.

Now, the present invention will be described more specifically below with reference to working examples.

Example

Production of polymerizable liposome-forming lipid

Production of eleostearic acid anhydride

The amount of tung oil fatty acid equivalent to 80 g of eleostearic acid was dissolved in 600 ml of carbon tetrachloride fresh from dehydration and distillation. The solution admixed wit 32.6 g of dicyclohexyl carbodiimide was tightly sealed in a container from which the entrapped air had been displaced with argon gas in advance. The mixture in the container was left standing (with occasional stirring) at 25° C. for 24 hours. It was filtrated to separate insolubles. The filtrate was evaporated to dryness. When the dry residue was refined by a silica gel chromatography using dichloromethane as an eluent, oleostearic acid anhydride was obtained in a yield of 29%.

Production of cadmium complex of egg yolk lecithin (phosphatidyl choline) hydrolyzate In 450 ml of dehydrated ether, 45 g of egg yolk lecithin (QP Co. PL-100) was dissolved. The resultant solution was filtrated to separate insolubles. The filtrate admixed with 50 ml of methanol solution containing tetrabutyl ammonium hydroxide in a concentration of 10% was vigorously shaken at a temperature of 25° C. When the reaction proceeded to a point where the solution caused precipitation of suspended particles and brought out gradual phase separation, the reaction mixture was left standing at rest until a brown oily substance was thoroughly allowed to settle. Then, the supernatant was separated by decantation. The brown oily substance was washed three times with 100 ml of dehydrated ether. The washed substance was dissolved in 125 ml of dehydrated methanol by heating. The solution was refluxed at the boiling point thereof and admixed with 1 g of a decolorizing agent and filtrated hot. The filtrate was cooled and combined with 250 ml of dehydrated ether. After the precipitate settled, the resultant supernatant was removed by decantation. The remaining precipitate was dissolved in 40 ml of boiling water. The solution and a solution of 8 g of 5/2 hydrate of cadmium chloride in 20 ml of pure water added thereto were refluxed at the boiling point in the presence of 2.5 g of activated carbon and 2 g of decolorizing agent. The reaction mixture was passed through a filter paper and a Millipore filter of 0.25 μm. When the filtrate was mixed with 100 to 150 ml of ethanol, there occurred a colored precipitate. The sediment was removed and the turbid solution was separated. When the turbid solution was vigorously shaken with 100 to 150 ml of ethanol, white crystals were precipitated. The solution was left standing overnight at a temperature of 0° to 5° C., and the crystals separated therein were collected. The crystals were washed with dehydrated methanol, dehydrated ether, and dehydrated benzene in the order mentioned and further vacuum dried over phosphorus pentoxide at a temperature of 80° C. Consequently, cadmium complex of phosphatidyl choline hydrolyzate was obtained in a yield of 56%.

Production of polymerizable lipid by esterification stirring, 6.74 g of the cadmium complex of egg yolk lecithin hydrolyzate was suspended in 160 ml of chloroform fresh from distillation. The suspension was mixed with 24.70 g of tung oil fatty acid anhydride and 5.61 g of 4-dimethyl aminopyridine as a catalyst. The mixture was placed in a container, which had the entrapped air displaced with argon gas and then was tightly stoppered. In a dark place, the mixture in the container was stirred for reaction at 25° C. for 60 hours. The reaction mixture was filtrated to separate white insolubles which had been precipitated in the reaction. It was then subjected to evaporation at room temperature to expel the solvent. The residue was dissolved in 100 ml of a mixed solvent comprising of methanol, chloroform, and water at a ratio of 5/4/1. The resultant solution was filtrated and the filtrate was passed through a column of ion-exchange resin, AG-501-X8 (D) (Bio-Rad). The adsorbate was eluted with 500 ml of the mixed solvent. The eluate was subjected to evaporation at 25° C. The redisue was dissolved in chloroform and purified by the use of a silica gel column. Consequently, oleostearic acid phosphatidyl choline was obtained in a yield of 30%. The infrared absorption spectrum of this product is shown in FIG. 1.

Production of hydrolyzate of Cephalin and esterification thereof 5.0 g of L-α- Phosphatidyl ethanolamine (cephalin, Sigma, Type II-S) was dissolved in 50 ml of dry ether, 6 ml of 10% methanol solution of tetrabutyl ammonium hydroixde was added into the solution thus formed and then it was vigorously stirred. Precipitate thus formed was washed with 20 ml of dry ether for three times and then dissolved in 15 ml of dry methanol. Dry ether was added to the solution thus obtained to form precipitate again and was subjected the upper layer to decantation. The precipitate was dried on phosphorus pentoxide at 25° C. for 24 hours. Into 1.40 g of hydrolyzate of cephalin thus obtained, 70 ml of chloroform fresh from distillation, 10.53 g tung oil fatty acid anhydride and 2.39 g of 4-dimethyl aminopyridine were added and the subjected to esterification reaction and purification by the same method as those of lecithin. Finally, cephalin fraction was recovered by silica gel column chromtography and dieleostearyl phosphatidyl ethanolamine in 10% of yield. Rf value of silica gel TLC (CHCl$_3$/MeOh/H$_2$O=65/25/4) is 0.37, while Rf volue of phosphatidyl choline was 0.19.

Production of hydrolyzate of phosphatidyl serine and esterification thereof

In the same method as that of hydrolyzate of cephalin and esterification thereof, 5.0 g of L-α-phosphatidly-L-serine (Sigma, Brain extract, Type III containing 80-85% of phosphtidly serine) was used instead of the cephalin and hydrolyzation and esterification with tung oil fatty acid was carried out to obtain dieleostearoyl phosphatidyl serine. Rf volue of silica gel TLC (CHCl$_3$/MeOH/H$_2$O=65/25/4) was 0.17.

Production of liposome from polymerizable phospholipid

In 6 ml of chloroform, 200 mg of the oleostearic acid phosphatidyl choline was dissolved. The lipid solution so obtained was placed in a flask shaped like an eggplant and treated with an evaportor for the solvent to be thoroughly expelled and for the lipid to be deposited in the form of thin layer on the bottom surface of the flask. The lipid layer and 10 ml of Hepes buffer (10 mM, ph 8.0) added thereto were shaken by a vortex mixer and then treated with a tip type ultrasonic irradiator (40 to 50 W) for 10 minutes under a flow of argon. By this treatment, the liquid under treatment was transformed from a turbid liquid into a clear dispersion, evincing the formation of liposomes. Under a scanning electron microscope, the dispersion was observed to contain spherical particles 0.2 to 0.5 μm in diameter, again evincing the formation of liposomes.

Polymerization of liposomes (preparation of medical carrier)

The liposomes of a concentration of 10 mg/ml was placed in a water bath kept at 25° C. and irradiated with the ultraviolet light emitted from a mercury vapor lamp of 75 W disposed at a distance of 12 cm. During the course of this irradiation, the absorbance at 272 nm due to a conjugated triene decreased with elapse of time, evincing the progress of polymerization.

Preparation of capsulated hemoglobin with liposomes

A solution was obtained by adding chloroform solution containing 22.4 mg (58 μ.mol) of cholesterol and chloroform solution containing 2.4 mg (8.5 μ.mol) of tung oil fatty acid to 46 mlg (58 μ.mol) of the eleostearic acid phosphatidyl choline obtained in the aforementioned experiment on the production of polymerizable liposome-forming lipid. The solution so obtained was placed in an eggplant-shaped flask having an inner volume of 50 ml and blown with nitrogen gas until a film was formed on the bottom surface of the flask. The film was treated with an evaporator for one hour at a temperature of 25° C. until the film was dried, and thereafter subjected to vacuum drying for 2.5 hours at a temperature of 25° C. The dry film and 10 ml of physiological saline solution containing 10% of hemoglobin treated in advance with carbon monoxide were shaken in a Vortex mixer and then treated with a bath type ultrasonic irradiator (20 W) for 30 minutes under a flow of argon. The resultant dispersion and 40 ml of phosphate buffer (pH 7.4) added thereto from the centrifugation was combined with 11 ml of phosphate buffer (pH 7.4).

A 3.5-ml portion of the resultant suspension was placed in a container and, after displacement of the inner atmosphere with carbon monoxide, stirred overnight in a dark place, then centrifuged at 5,000 rpm for 10 minutes, and diluted by addition of phosphate buffer (pH 7.4) to a total volume of 3 ml to afford a monomeric liposome suspension. A 0.4-ml portion of this monomeric liposome suspension was added to 3.6 ml of bovine blood plasma or phosphate buffer.

A 3.5-ml portion of the resultant suspension was placed in a container and, after displacement of the inner atmosphere with carbon dioxide, stirred at a temperature of 25° C. for 12 hours and simultaneously irradiated with the ultraviolet light from a mercury vapor lamp of 75 W disposed at a distance of 12 cm from the sample, and then centrifuged at 5,000 rpm for 10 minutes. The sediment resulting from the centrifugation was diluted by addition of phosphate buffer (pH 7.4) to a total volume of 3 ml to afford a polymeric liposomes suspension. A 0.4-ml portion of this polymeric liposomes suspension was added to 3.6 ml of bovine blood plasma or phosphate buffer. Test for leakage of hemoglobin The monomer and polymer samples of hemoglobin liposomes were left standing in boving blood plasma and phosphate buffer for a prescribed length of time. The visible spectra (peaks near 400 nm due to hemoglobin) of the whole suspensions and those of the supernatants obtained by centrifuging the whole suspensions (bovine blood plasma 10,000 rpm and phosphate buffer 5,000 rpm, each for 10 minutes) were compared to determine leakage of hemoglobin from liposomes. The results are shown in Table 1. Control 1

Capsules of hemoglobin with liposomes were prepared by following the procedure of Experiment on polymerization of liposomes, using 45 mg (60 μ.mol) of diene phosphatidyl represented by the following chemical formula, 23.2 mg (60 μ.mol) of cholesterol, and 2.4 mg (8.5 μ.mol) of tung oil fatty acid.

It is noted from Table 1 that leakage of hemoglobin from eleostearic acid phosphatidyl choline monomeric liposome in bovine blood plasma increased with elapse of time and that absolutely no leakage of hemoglobin from polymeric liposome was detected even after one week's standing, indicating conspicuous improvement in the stability of liposome by polymerization. From Table 2, it is noted that in the diene phosphatidyl choline system, leakage of hemoglobin even from polymeric liposomes was detected, showing poor effect of polymerization.

As described above, since the polymerizable liposome-forming lipid of the present invention contains in the hydrophobic groups thereof three conjugated double bonds originating in eleostearic acid as shown in the general formula I, the monomeric liposome formed from the lipid is readily polymerized by irradiation with ultraviolet light and the polymerized liposome enjoys enhanced stability as compared with the liposome formed solely of natural phospholipid. Highly desirable medicinal substances, artificial red cells, etc., therefore, are obtained by depositing meidicinal substances, enzymes, hemoglobin, etc. on the polymeric liposomes formed from the polymerizable liposome-forming lipid of the present invention.

Further, since the method of the present invention for the production phosphatidyl choline of the polymerizable. liposome-forming lipid comprises causing tung oil fatty acid containing at least 60% by weight of eleostearic acid to be esterified with the hydrolyzate of phospholipid, it can be effected by using a fatty acid derived from natural oil. It has no use for the step for synthesis of unsaturated fatty acid which is indispensable to the conventional method. Thus, the method permits a generous reduction in the number of steps of process. It also produces the lipid in a yield more than 10 times the conventional level. The product, therefore, is obtained far less expensively.

TABLE 1

| Elapsed time | Kind of liposome | In bovine blood plasma (relative value) | | | In phosphate buffer (relative value) | | |
| --- | --- | --- | --- | --- | --- | --- | --- |
| | | Total amount of Hb | Leakage amount of Hb | Leakage ratio (%) | Total amount of Hb | Leakage amount of Hb | Leakage ratio (%) |
| 4 hrs | monomer | 5.05 | 1.38 | 27 | 3.76 | 0.40 | 11 |
| 4 hrs | polymer | 3.18 | 0 | 0 | 2.38 | 0 | 0 |
| 3 days | monomer | 4.14 | 1.32 | 32 | 3.67 | 0.43 | 12 |
| 3 days | polymer | 2.17 | 0 | 0 | 1.96 | 0 | 0 |
| 1 week | monomer | 3.68 | 1.57 | 43 | 3.88 | 0.48 | 12 |
| 1 week | polymer | 2.51 | 0 | 0 | 2.18 | 0 | 0 |

TABLE 2

| Elapsed time | Kind of liposome | In bovine blood plasma (relative value) | | | In phosphate buffer (relative value) | | |
|---|---|---|---|---|---|---|---|
| | | Total amount of Hb | Leakage amount of Hb | Leakage ratio (%) | Total amount of Hb | Leakage amount of Hb | Leakage ratio (%) |
| 4 hrs | monomer | 13.31 | 4.26 | 32 | 13.10 | 1.05 | 8 |
| 4 hrs | polymer | 12.49 | 4.18 | 33 | 13.09 | 1.09 | 8 |
| 3 days | monomer | 13.38 | 6.50 | 49 | 10.09 | 0.39 | 4 |
| 3 days | polymer | 12.10 | 3.52 | 29 | 11.85 | 1.84 | 15 |
| 1 week | monomer | 11.79 | 5.40 | 46 | 7.82 | 0.15 | 2 |
| 1 week | polymer | 11.02 | 2.89 | 26 | 8.86 | 0.72 | 8 |

Hb: hemoglobin

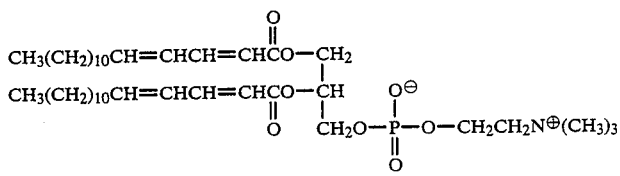

The monomer and polymer samples of hemoglobin liposome consequently obtained were tested for leakage of hemoglobin by following the procedure of Experiment on polymerization of liposomes. The results are shown in Table 2.

What is claimed is:

1. A polymerizable liposome-forming lipid represented by the general formula I:

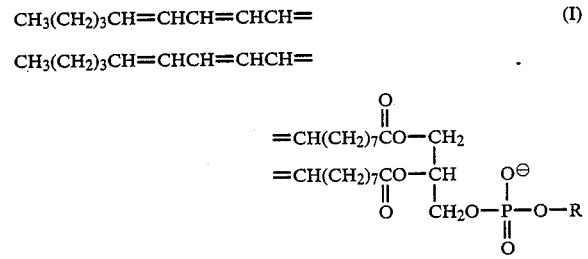

wherein R stands for $-(CH_2)_2N^{\oplus}(CH_3)_3$.

2. A method for the production of a polymerizable liposome-forming lipid represented by formula I:

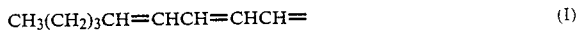
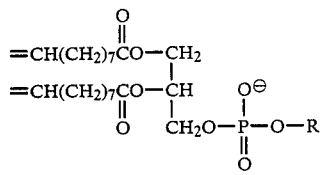

wherein R stands $-(CH_2)_2N^{\oplus}(CH_3)_3$, said method comprising esterifying 100 parts by weight of a hydrolyzate of phosphatidyl choline, cephalin or phosphatidyl serine with 200 to 400 parts by weight of tung oil fatty acid containing at least 60% by weight of oleostearic acid in the form of an acid anhydride at a temperature in the range of 15° to 25° C.

3. The method according to claim 2, wherein said hydrolyzate is a hydrolyzate of phosphatidyl choline.

4. A method according to claim 2, wherein said hydrolyzate of phosphatidyl choline is the hydrolyzate of egg yolk lecithin.

* * * * *